United States Patent
Anand et al.

(10) Patent No.: US 9,399,148 B2
(45) Date of Patent: Jul. 26, 2016

(54) MR IMAGING GUIDED THERAPHY

(75) Inventors: Ajay Anand, Fishkill, NY (US); Gosta Jakob Ehnholm, Helsinki (FI); Balasundar Iyyavu Raju, Chester, NY (US)

(73) Assignee: Koninklijke Philips N.V., Eindhoven (NL)

(*) Notice: Subject to any disclaimer, the term of this patent is extended or adjusted under 35 U.S.C. 154(b) by 792 days.

(21) Appl. No.: 13/321,238

(22) PCT Filed: Jun. 2, 2010

(86) PCT No.: PCT/IB2010/052458
§ 371 (c)(1),
(2), (4) Date: Mar. 23, 2012

(87) PCT Pub. No.: WO2010/140125
PCT Pub. Date: Dec. 9, 2010

(65) Prior Publication Data
US 2012/0172708 A1    Jul. 5, 2012

Related U.S. Application Data (60) Provisional application No. 61/183,121, filed on Jun. 2, 2009, provisional application No. 61/265,771, filed on Dec. 2, 2009.

(51) Int. Cl.
*A61N 7/00*  (2006.01)
*A61B 8/00*  (2006.01)
(Continued)

(52) U.S. Cl.
CPC .............. *A61N 7/02* (2013.01); *A61B 8/5223* (2013.01); *A61B 2017/00084* (2013.01);
(Continued)

(58) Field of Classification Search
CPC ................. A61B 8/5223; A61B 2017/00084; A61B 2019/5236; A61B 2019/5276; A61N 7/02; A61N 2007/0078; A61N 2007/0008

USPC .......... 600/412, 411, 447, 438, 439; 606/1–3, 606/20, 28, 41; 702/102
See application file for complete search history.

(56) References Cited

U.S. PATENT DOCUMENTS 5,984,881 A * 11/1999 Ishibashi ............ A61B 17/2256
                                                              601/2
6,445,183 B1 * 9/2002 Shimizu et al. ............... 324/309
(Continued)

FOREIGN PATENT DOCUMENTS

| FR | 2798296 A1 | 3/2001 |
| WO | 03096883 A2 | 11/2003 |
| WO | 2008152542 A2 | 12/2008 |

OTHER PUBLICATIONS

Salomir R et al: "Local Hyperthermia With MR-Guided Focused Ultrasound: Spiral Trajectory of the Focal Point Optimized for Temperature Uniformity in the Target Region" target region. Journal of Magnetic Resonance Imaging : vol. 12, No. 4, Oct. 2000, pp. 571-583.

(Continued)

*Primary Examiner* — Long V Le
*Assistant Examiner* — Colin T Sakamoto (57) ABSTRACT

The invention relates to a therapeutic system which comprises an ultrasound therapy unit (1, 518) arranged to insonify at least a portion of a body (2, 508) of a patient with high intensity ultrasound and a MR imaging unit (3, 500) arranged to acquire MR signals from the portion of the body (2, 508) and to reconstruct a thermographic MR image from the MR signals. It is an object of the invention to enable MR guided high intensity focused ultrasound (HIFU) treatment, in which temperature values within critical anatomic regions containing fat can be monitored. The invention proposes that the therapeutic system further comprises an ultrasound diagnostic unit (5, 518) which is arranged to acquire ultrasound signals from the portion of the body (2, 508) and to derive at least one local temperature value from the ultrasound signals.

15 Claims, 5 Drawing Sheets

(51) Int. Cl.
*A61B 5/055* (2006.01)
*A61N 7/02* (2006.01)
*A61B 8/08* (2006.01)
*A61B 17/00* (2006.01)
*A61B 19/00* (2006.01)

(52) U.S. Cl.
CPC ...... *A61B 2019/5236* (2013.01); *A61B 2019/5276* (2013.01); *A61N 2007/0008* (2013.01); *A61N 2007/0078* (2013.01)

(56) References Cited

U.S. PATENT DOCUMENTS

| | | | |
|---|---|---|---|
| 6,508,774 | B1 | 1/2003 | Acker et al. |
| 6,618,608 | B1* | 9/2003 | Watkins et al. ............... 600/412 |
| 6,623,430 | B1 | 9/2003 | Slayton et al. |
| 7,699,780 | B2 | 4/2010 | Vitek et al. |
| 7,771,418 | B2* | 8/2010 | Chopra ................. A61B 5/055 606/27 |
| 8,251,908 | B2* | 8/2012 | Vortman ............... A61B 8/4245 600/407 |
| 2003/0036706 | A1* | 2/2003 | Slayton et al. ................ 600/439 |
| 2005/0240127 | A1 | 10/2005 | Selp et al. |
| 2005/0281313 | A1* | 12/2005 | Qian et al. ..................... 374/117 |
| 2006/0052699 | A1 | 3/2006 | Angelsen et al. |
| 2006/0058671 | A1* | 3/2006 | Vitek et al. .................... 600/447 |
| 2006/0206105 | A1* | 9/2006 | Chopra et al. ................. 606/27 |
| 2007/0106157 | A1* | 5/2007 | Kaczkowski et al. ........ 600/438 |
| 2008/0039746 | A1 | 2/2008 | Hissong et al. |
| 2008/0058634 | A1* | 3/2008 | Roland et al. ................. 600/411 |
| 2008/0107150 | A1* | 5/2008 | Brummel et al. ............. 374/119 |
| 2008/0194941 | A1 | 8/2008 | Steinmeyer et al. |
| 2009/0069667 | A1* | 3/2009 | Lindstrom et al. ........... 600/411 |
| 2009/0112132 | A1* | 4/2009 | Chang et al. ..................... 601/3 |
| 2009/0182223 | A1* | 7/2009 | Dai et al. ...................... 600/411 |
| 2009/0312637 | A1 | 12/2009 | Raju et al. |
| 2010/0076352 | A1 | 3/2010 | Kim et al. |
| 2010/0125192 | A1* | 5/2010 | Chopra et al. ................ 600/411 |

OTHER PUBLICATIONS

Dhiraj Arora et al: "Control of Thermal Therapies With Moving Power Deposition Field"; Physics in Medicine and Biology, Taylor and Francis Ltd. London, GB LNKDDOI: 10.1088/0031-9155/51/5/011, vol. 51, No. 5, Mar. 7, 2006, pp. 1201-1219.

Pernot, M.F. et al., "In-vivo non-invasive motion tracking and correction to high intensity focused ultrasound therapy", Annual International Conference of the IEEE Engineering in Medicine and Biology Proceedings, 2006, Abstract.

Pernot, M.F. et al., "Feasibility of real-time motion correction for H.I.F.U applications", Proceedings of the IEEE Ultrasonics Symposium, 2003, Abstract.

Berriet, R. et al., "Design of piezocomposite matrix transducer configuration for multi-mode operation in HIFU applications", Proceedings IEE Ultrasonics Symposium, 2007, Abstract.

Salomir, R. et al., "Automatic feedback control of the temperature for MRI guided therapeutic ultrasound", Engineering in Medicine and Biology Society, 2007, 29th Annual International Conference of the IEEE, Aug. 22-26, 2007, Abstract.

Miller, N.R. et al., "Ultrasonic measurement of the temperature distribution due to absorption of diagnostic Ultrasound: potential and limitations", Journal of Physics: Conference Series 1 (2004), Abstract.

Armin, V. et al., "HIFU therapy planning using pre-treatment imaging and simulation", AIP Conference Proceedings, 2006.

* cited by examiner

MR IMAGING GUIDED THERAPHY

CROSS REFERENCE TO RELATED CASES

Applicants claim the benefit of Provisional Applications Ser. Nos. U.S. 61/183,121, filed 2 Jun. 2009, and U.S. 61/265,771, filed 2 Dec. 2009.

FIELD OF THE INVENTION

The invention relates to the field of magnetic resonance (MR) imaging. It concerns a therapeutic system comprising an ultrasound therapy unit and a MR imaging unit. Moreover, the invention relates to a computer-readable storage medium and to a method of monitoring a high intensity ultrasound therapeutic action.

BACKGROUND OF THE INVENTION

A therapeutic system comprising an ultrasound therapy unit and a MR imaging unit is generally known, e.g., from WO 2008/152542 A2.

Ultrasound is becoming an increasingly desirable approach for specific therapeutic interventions. In particular, the use of high intensity focused ultrasound is currently being used as an approach for thermal therapeutic intervention for uterine fibroids and has been examined for possible uses in the treatment of liver, brain, prostate, and other cancerous lesions. Ultrasound has also been the subject of much research as a means for mediating clot dissolution (sono-thrombolysis), and has been shown to increase the efficacy of existing medical treatments such as the use of tissue plasminogen activator (tPA) as a thrombolytic agent for stroke patients. Ultrasound mediated drug delivery and gene therapy is a further active area of research. Genetic expression of proteins in gene therapy and increased delivery of drugs in site-targeted therapies have potential to treat a wide variety of diseases with minimal side-effects. Another application for ultrasound therapy is non-invasive treatment for cosmetic means, e.g., removal of fat. The use of ultrasound in all of these applications is desirable because it allows the non-invasive treatment of deep tissues with little or no effect on overlying organs.

Ultrasound therapy for tissue ablation works by insonifying a tissue of interest with high intensity ultrasound that is absorbed and converted into heat, thereby raising the temperature of the respective tissues. As the temperature rises above 55 degree centigrade, coagulative necrosis of the tissues occurs resulting in immediate cell death. The transducers used in therapy can be outside the body or be inserted into the body e.g. through blood vessels, urethra, rectum etc. However, ultrasound therapy is not limited to tissue ablation, but also relates to the use of other types of ultrasound-based bio-effects, including hemostasis, drug or gene delivery, clot dissolution etc.

Nowadays, MR imaging guided high intensity focused ultrasound (MR HIFU) systems are commercially available. The first clinical application is the ablation of benign tumours in the uterus, so-called intrauterine fibroids. Therein a focused ultrasound beam is directed towards the abdomen. The ultrasound beam is used for heating a tumour through the skin and intervening tissue while MR imaging is used for monitoring the temperature distribution within the insonified region. The latter makes the procedure safe and efficient.

MR thermometry, based on the proton resonance frequency shift (PRFS) in water, is considered the 'gold standard' in the non-invasive monitoring of such ablative thermal therapies. Using the PRFS method the temperature in tissues having a high water content can be monitored accurately. A linear shift of the proton resonance frequency is observed for the range of temperatures being used in HIFU. In this range MR thermometry is also reasonably sensitive. The reconstruction of thermographic MR images during ultrasound therapy is useful to provide feedback to ensure that adequate heating is accomplished at the intended location while safeguarding that other critical anatomic structures are left intact.

A drawback of MR thermometry is that tissues containing fat cannot be monitored. This is because the PRFS in fat is essentially independent of temperature. An example of this is the subcutaneous fat layer. For example, patients being treated for intrauterine fibroids usually have a fat layer under the skin of up to a few centimeters. The focused ultrasound beam used to ablate deep seated tissues has to pass through this layer. The fat, having both lower heat conductivity and no vascularity, is easily overheated. For many patients this becomes a risk, limiting the usefulness and applicability of the MR HIFU method.

From the foregoing it is readily appreciated that there is a need for an improved therapeutic system for MR imaging guided HIFU. It is consequently an object of the invention to enable the detection of unintended sites of possible thermal damage, thereby improving the safety of the therapeutic procedure.

SUMMARY OF THE INVENTION

The invention provides for a therapeutic system, a computer-readable storage medium, and a method of monitoring a high intensity ultrasound therapeutic action in the independent claims. Embodiments are given in the dependent claims.

As used herein MR is an abbreviation for magnetic resonance. As used herein HIFU is an abbreviation for high intensity focused ultrasound.

In accordance with the invention a therapeutic system is disclosed. The system of the invention comprises:

an ultrasound therapy unit arranged to insonify at least a portion of a body of a patient with high intensity ultrasound;

a MR imaging unit arranged to acquire MR signals from the portion of the body and to reconstruct a thermographic MR image from the MR signals;

an ultrasound diagnostic unit arranged to acquire ultrasound signals from the portion of the body and to derive at least one local temperature value from the ultrasound signals. The ultrasound therapy unit and the ultrasound diagnostic unit may be separate units or the ultrasound therapy unit may comprise the ultrasound diagnostic unit.

MR signals as used herein are understood to be measurements or other representations of radio frequency signals emitted by atomic spins in the portion of the body during the acuisition of an image by the MR imaging unit. These MR signals may be reconstructed into images.

The process of insonification as used herein is understood to be a synonym with the term sonication. Sonication as used herein is defined to be the act of disrupting or deactivating a biological material by applying ultrasound to agitate the biological material.

The gist of the invention is the combination of ultrasound thermometry with MR thermometry to obtain temperature images not only in the tissues having high water content but also in critical areas of the treated portion of the body containing fat.

The derivation of local temperature values from acquired ultrasound signals is also referred to as ultrasound thermometry. Ultrasound thermometry has been demonstrated to enable temperature imaging for temperatures ranging up to 50 to 60 degrees centigrade. When a region of tissue is heated, the resulting temperature rise results in local variations in the speed of sound and thermal expansion. The sound speed for aqueous tissues initially increases with temperature up to 50 degree centigrade, reaches a plateau and then decreases at higher temperatures. The lack of sensitivity to temperatures close to 50 degree centigrade results in erroneous estimates. At higher temperatures multi-valued estimates may occur. For fat tissue the ultrasound speed decreases with temperature. For temperature rises on the order of 10 to 15 degree centigrade above body temperature, the effect of thermal expansion is small compared to the ultrasound speed change. Ultrasound thermometry can detect local temperature rises up to 10 to 15 degree centigrade in both aqueous and fatty tissues with an accuracy of approximately 1 degree centigrade.

Ultrasound thermometry is implemented by the so called echo-shift method. In a simple embodiment, using a single ultrasound transducer, an ultrasound echo signal is received, e.g. from the same transducer that generated the sonic pulse, and registered during a time sufficiently long for the pulse to travel to the farthest distance to be monitored, and back. After a short time interval, another pulse is transmitted through the heated region and received. The two signals are compared to determine the echo shift. The echo shift is converted into the corresponding value of the temperature change using well established methods. Methods of ultrasound thermometry are known by which two- and three-dimensional temperature maps can be obtained.

In an embodiment of the invention the MR imaging unit is adapted for acquiring the MR signals from within an imaging zone. Typically magnetic resonance imaging units comprise a magnet, gradient coils and antennas or coils for sending and receiving radio frequency signals in order to acquire magnetic resonance signals from the portion of the body. The imaging zone is the region of the magnetic field of the magnetic resonance imaging unit that is uniform enough for acquiring magnetic resonance signals which are able to be reconstructed into a magnetic resonance image. The ultrasound therapy unit is adapted to insonify a target zone within the patient. The at least a portion of a body of a patient which is insonified with the ultrasound therapy unit is located within the target zone.

The ultrasound therapy unit comprises a multi-element ultrasonic transducer adapted for focusing ultrasound at the target zone. A multi-element ultrasonic transducer has multiple ultrasonic elements which may produce ultrasound. By controlling the amplitude and phase emitted from each of the elements of the multi-element ultrasonic transducer ultrasound may be focused or directed to a specific target zone within the patient. The therapeutic system further comprises a patient support adapted for receiving a patient. The patient support comprises an ultrasound window adapted for transmitting ultrasound from the multi-element ultrasonic transducer to the patient.

The multi-element ultrasonic transducer may be located within a chamber under the patient support which is filled with an ultrasound conducting medium. For example degassed water may be used to immerse the multi-element ultrasonic transducer. The ultrasonic transducer has a near field region located between the transducer and the target zone. The imaging zone comprises the near field region. This means that the MR imaging unit is able to acquire MR signals from the near field region. The at least one local temperature value is measured within the near field region. This means that the ultrasonic diagnostic unit makes a temperature measurement in the near field region. The ultrasound diagnostic unit therefore may be used to monitor the temperature in the near field region.

The therapeutic system further comprises a computing device for controlling the MR imaging unit, the ultrasound diagnostic unit and the ultrasonic therapy unit. The computing device comprises one or more processors. The computing device further comprises memory. The computing device comprises one or more programs stored in the memory. The one or more programs are configured to be executed by the one or more processors. The one or more programs comprise instructions for receiving a treatment plan for insonification of the target zone. The one or more programs further comprise instructions for predicting the attenuation of ultrasound energy in the near field region using the MR signals and the at least one local temperature. The attenuation of ultrasound energy in the near field region may be determined by noting the temperature increase in the near field region during a test shot. A test shot is when the ultrasound therapy unit is used to insonify the target zone at a reduced power. The detection of an increase in the temperature of the near field region that is larger than expected or larger than a predetermined temperature increase may indicate an obstruction or a region which attenuates ultrasound more than was expected. This is advantageous, because it may not be possible to accurately predict the attenuation of ultrasound energy in the near field region using a model. For instance one may use magnetic resonance or other imaging techniques to image the subject and create the treatment plan. This may or may not accurately predict the attenuation of ultrasound energy. By using the MR thermographic image and the at least one local temperature attenuation of ultrasound in the near field region may be detected. The one or more programs further comprise instructions for adjusting the treatment plan based upon the prediction of attenuation of ultrasound energy in the near field region. This adjustment of the treatment plan may be the adjustment of the amplitude and/or phase applied to each element of the multi-element ultrasonic transducer.

In another embodiment the near field region comprises sub-near field regions. There is a sub-near field region corresponding to each element of the multi-element ultrasonic transducer. The sub-near field region is the near field region adjacent to each element of the multi-element ultrasonic transducer. The one or more programs further comprise instructions for predicting the attenuation of ultrasound energy in each of the sub-near field regions using the MR thermographic image and at least one local temperature. The MR thermographic image and the local temperature as measured by the ultrasound diagnostic unit may be used to determine a temperature increase in the sub-near field region. A temperature increase in a sub-near field region that is greater than expected or greater than a predetermined temperature increase may indicate attenuation in the sub-near field region.

In another embodiment the one or more programs further comprise instructions for adjusting the frequency of ultrasound energy emitted by each element (522, 524, 526) of the multi-element ultrasonic transducer which is predicted to have an attenuation of ultrasound in its corresponding sub-near field region greater than a predetermined value. For instance if there is an obstruction in a particular sub-near field region it may be possible to reduce the effect of the obstruction by reducing the frequency of the ultrasound energy, because the ultrasound becomes less focused. The attenuation of ultrasound in tissue is frequency dependent. Therefore adjusting the frequency may allow a reduction in the attenuation of ultrasound in the particular sub-near field region.

In another embodiment the one or more programs further comprise instructions for adjusting the aperture of the multi-element ultrasonic transducer by reducing the amplitude of ultrasound energy emitted by each element of the multi-element ultrasonic transducer which is predicted to have an attenuation of ultrasound in its corresponding sub-near field region greater than a predetermined value. If the attenuation of ultrasound in a sub-near field region is too large then the corresponding element of the multi-element ultrasonic transducer may either be deactivated or reduce the amplitude of the ultrasound emitted by that element. Remaining elements of the multi-element ultrasonic transducer which do not experience abnormal attenuation in their sub-near field region may be used to focus ultrasound into the target zone.

In another embodiment the aperture of the multi-element transducer is formed by non-contiguous elements of the multi-element ultrasonic transducer. The active elements of the multi-element transducer may be contiguous, but it is not a requirement. For instance if there is a local obstruction, such as a bone, in a particular sub-near field region the obstruction may be avoided by deactivating a single element of the multi-element ultrasonic transducer.

In another embodiment the apparatus further comprises a display adapted for displaying a graphical representation of the multi-element ultrasonic transducer. The display is further adapted for graphically representing the subnear field region of each element of the multi-element ultrasonic transducer. The display is adapted for indicating which of the sub-field regions is predicted to attenuate ultrasound energy. The apparatus further comprises a user interface adapted for receiving a selection of the elements of the multi-element transducer to use during insonification of the target zone. A user may use the user interface to select which elements are used. Alternatively the user may also indicate that certain elements operate at a reduced amplitude.

In another embodiment the apparatus further comprises a signaling element adapted for signaling an operator when the attenuation of the ultrasound in the near field region is greater than a predetermined threshold. This is beneficial because if the attenuation of ultrasound in a near field region is greater than a predetermined threshold it may indicate that there is a problem with the treatment plan. It may be advantageous for an operator or healthcare provider to inspect the treatment plan instead of proceeding automatically.

In another embodiment the one or more programs further comprise instructions for predicting the attenuation of ultrasound in the near field region by measuring an increase in temperature in the near field region using magnetic resonance thermometry during a test shot of the ultrasonic system. Magnetic resonance thermometry is used to construct the thermographic MR image.

In another embodiment the one or more programs further comprise instructions for predicting the attenuation of ultrasound in the near field region by measuring an increase in temperature in the near field region using the at least one local temperature value from the ultrasound signals. In this embodiment the ultrasound diagnostic unit is used to determine the increase in temperature in the near field region. In another embodiment the near field region comprises the vicinity of the ultrasound window. This is advantageous because there may be bubbles at the interface between the ultrasound window and the patient. Bubbles have the ability to scatter or to absorb large amounts of ultrasound energy. For instance cavitation of a bubble may result in a large attenuation of ultrasound energy. This may generate heat which can be damaging to the surface or skin of a patient. In this way bubbles may be detected in the vicinity of the ultrasound window.

In accordance with a preferred embodiment of the invention, the MR imaging unit of the therapeutic system is arranged to monitor the spatial temperature distribution within water containing tissue of the treated portion of the body, while the ultrasound diagnostic unit is arranged to monitor the local temperature within fat tissue. By combining ultrasound thermometry for monitoring the temperature in fat tissue with MR thermometry for monitoring the temperature of tissue containing water, a complete map of the temperature distribution is obtained for safe and practical use. By means of MR imaging the destruction of the tumour is monitored. Simultaneously, the safety in watery tissues is ensured. Ultrasound thermometry is used to monitor that the temperature within regions containing fat tissue does not exceed safe limits. For this purpose, the ultrasound diagnostic unit of the system of the invention is preferably arranged to automatically indicate when a preset temperature threshold value is exceeded. Since ultrasound diagnostic imaging is used to estimate temperature rises outside the focus of the ultrasound therapy, i.e. in regions where the temperature rise is not expected to increase more than a couple of degrees centigrade, the ultrasound thermography method is used in the regime of its best sensitivity. However, it has to be noted, that in water containing tissues both MR thermometry and ultrasound thermometry give useful results. Therefore, the ultrasound thermometry method can be used to verify the results of MR thermometry. In this way, the operation of the therapeutic system is made more robust. At the same time, the temperature values obtained in water containing tissues by means of MR thermometry can be used for calibration of the temperature values derived from the acquired ultrasound signals.

In accordance with a further preferred embodiment of the invention, the therapeutic system comprises a control logic that shuts off the insonification of the ultrasound therapy unit when the local temperature value derived by the ultrasound diagnostic unit exceeds a temperature threshold value. In this way it is made sure that no dangerous overheating occurs in the tissues containing fat within the pass of the high intensity focused ultrasound beam.

According to yet a further preferred embodiment of the invention, the therapeutic system comprises a visualization unit which is arranged to produce an image of the portion of the body in which a spatial temperature distribution derived from the acquired ultrasound signals is superimposed on the thermographic MR image. In this way, the regions of fat tissue that require safety assessment can be monitored during therapy by means of one single image which is presented to the operator. Moreover, the system can be used to identify the regions of fat tissue that require safety monitoring from the MR images produced during the treatment planning phase.

According to still another preferred embodiment of the invention, the ultrasound probe of the ultrasound diagnostic unit is co-registered with the transducer of the ultrasound therapy unit. The transducer of the ultrasound therapy unit and the ultrasound diagnostic unit may be physically the same devices. No additional ultrasound probe is required. This is possible because the ultrasound diagnostic unit is required to scan the region of tissue within the beam propagation part of the transducer of the ultrasound therapy unit in one or more dimensions.

In another embodiment the ultrasound therapy unit is a high-intensity focused ultrasound unit.

In another embodiment the therapeutic system further comprises a computing device for controlling the MR imaging unit, the ultrasound diagnostic unit, and the ultrasound therapy unit. The computing device comprises one or more processors. The computing device further comprises memory. The computing device comprises one or more programs stored in the memory. The one or more programs are configured to be executed by the one or more processors. The one or more programs comprise instructions for insonifying at least a portion of the body of the patient with the high-intensity ultrasound. The one or more programs further comprise instructions for acquiring MR signals from the portion of the body. The one or more programs further comprise instructions for reconstructing a thermographic MR image from the MR signals. The one or more programs further comprise instructions for acquiring ultrasound signals from the portion of the body. The one or more programs further comprise instructions for deriving at least one local temperature value from the ultrasound signals.

In another aspect the invention provides for a computer-readable storage medium containing instructions that when executed by a computing device of a therapeutic system cause the computing device to perform a method of monitoring during a high-intensity ultrasound therapeutic action. A high-intensity ultrasound therapeutic action is the insonification of at least a portion of a body of a patient with high intensity ultrasound. A computer-readable storage medium may be any medium that is adapted for storing instructions executed by a processor. For example a computer-readable storage medium may be, but is not limited to: random access memory, flash memory, a hard drive, a solid state hard drive, and a floppy disk. The computing device comprises one or more processors for executing the instructions. The therapeutic system comprises an ultrasound therapy unit arranged to insonify at least a portion of the body of a patient with high-intensity ultrasound. The therapeutic system further comprises an MR imaging unit arranged to acquire MR signals from the portion of the body and to reconstruct a thermographic MR image from the MR signals, wherein the therapeutic system further comprises an ultrasound diagnostic unit arranged to acquire ultrasound signals from the portion of the body and to derive at least one local temperature value from the ultrasound signals. The method comprises insonifying the at least a portion of the body of the patient with high-intensity ultrasound. The method further comprises acquiring MR signals from a portion of the body of the patient using the MR imaging unit. The method further comprises reconstructing a thermographic MR image from the MR signals. The method further comprises acquiring ultrasound signals from the portion of the body using the ultrasound diagnostic unit. The method further comprises driving at least one local temperature value from the ultrasound signals.

By means of the system of the invention described thus far a method of monitoring a high intensity ultrasound therapeutic action can be carried out, the method including:

acquisition of MR signals from a portion of a body of a patient;

reconstructing a thermographic MR image from the MR signals;

acquisition of ultrasound signals from the portion of the body;

derivation of at least one local temperature value from the ultrasound signals.

The method of the invention can be advantageously carried out in most MR imaging guided HIFU systems in clinical use at present. To this end it is merely necessary to utilize a computer program by which the system is controlled such that it performs the above-explained method steps of the invention. The computer program may be present either on a data carrier (CD, DVD or USB stick) or be present in a data network so as to be downloaded for installation in a corresponding control unit of the therapeutic system.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings FIG. 1 schematically shows a therapeutic system of the invention.

DETAILED DESCRIPTION OF EMBODIMENTS

Like numbered elements in these figures are either equivalent elements or perform the same function. Elements which have been discussed previously will not necessarily be discussed in later figures if the function is equivalent.

Figure 1:
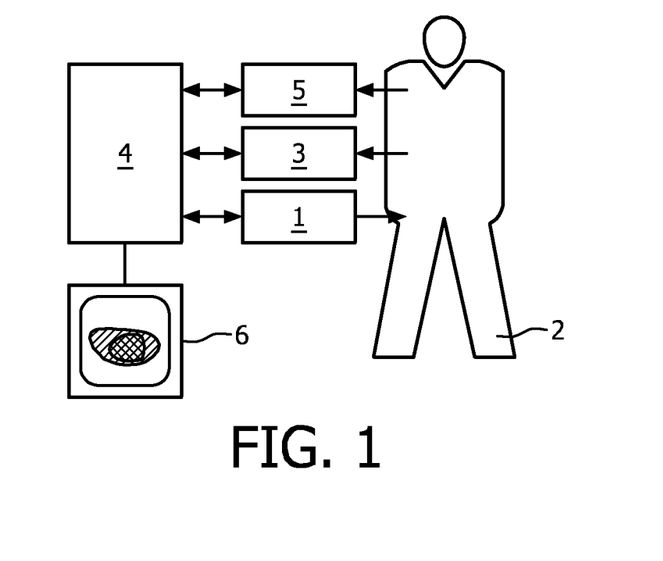

With reference to FIG. 1, the therapeutic system according to the invention comprises an ultrasound therapy unit 1 which is arranged to insonify at least a portion of a body 2 of a patient with a high intensity focused ultrasound beam. The system further comprises a MR imaging unit 3 that acquires MR signals from the portion of the body 2 and reconstructs thermographic MR images from the acquired MR signals on the basis of the local proton resonance frequency shift. The ultrasound therapy unit 1 and the MR imaging unit 3 are connected to a common control unit 4 of the system. Such a system is known, e.g., from the article "Local hyperthermia with MR-guided focused ultrasound: Spiral trajectory for the focal point optimized for temperature uniformity in the target region" by R. Salomir et al., Journal of Magnetic Resonance Imaging, vol. 12, 2000, pages 571-583). The control unit 4 controls the position, direction and/or focusing of the high intensity ultrasound beam. The control unit 4 processes data obtained via the MR imaging unit 3, for example during the treatment planning phase. Moreover, the control unit 4, which might be a micro computer as it is commonly used in medical imaging and therapeutic devices, computes a thermographic MR image, i.e. the spatial temperature distribution in the treated portion of the body 2 on the basis of the MR signals acquired via the MR imaging unit 3. The control unit may also be referred to as a computing device. The system is able to perform real-time MR thermography and—based on the measured and reconstructed temperature distribution—control the therapeutic action, i.e. causing the targeted elevation of local temperature in the tissue by means of suitably adjusting the focused ultrasound beam of the ultrasound therapy unit 1.

Further, provision is made for an ultrasound diagnostic unit 5 which is arranged to acquire ultrasound signals from the treated portion of the body 2 and to derive local temperature values from the received ultrasound signals. The transducer of the ultrasound therapy unit 5 is registered with the HIFU treatment transducer of the ultrasound therapy unit 1 and scans the region of tissue that occurs in the beam propagation path of the therapy transducer in one or more dimensions. A control logic is implemented in the control unit 4 that is designed to shut off the insonification of the ultrasound therapy unit 1 when the local temperature at a specific location within the body 2 exceeds a given temperature threshold value. In this way, the control unit 4 automatically ensures that no dangerous overheating especially in fat tissue of the body 2 occurs during ultrasound treatment. The temperature rise in the respective region of interest is monitored using ultrasound thermometry, wherein an image is generated by means of the control unit 4, in which the spatial temperature distribution derived from the acquired ultrasound signals is superimposed on the thermographic MR image. The combined image is presented via a display unit 6 to an operator of the system.

Figure 2:
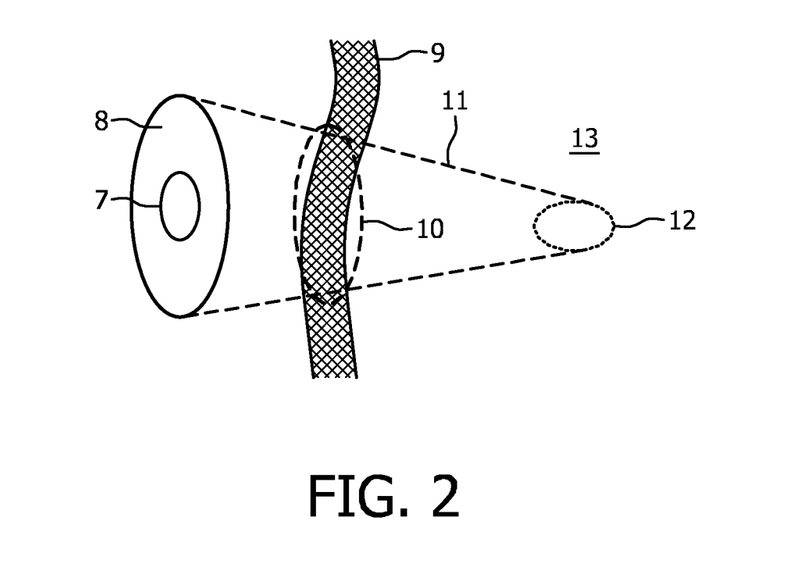
FIG. 2 shows a diagram illustrating the ultrasound based temperature monitoring in accordance with the invention.

With continuing reference to FIG. 1 and with further reference to FIG. 2, an ultrasound imaging probe 7 of the ultrasound diagnostic unit 5 is co-registered with a HIFU transducer 8 for use in the MR imaging environment of the system. Alternatively, the physically same ultrasound probe may be used for ultrasound imaging and therapy in a time-multiplexed mode. On the basis of MR planning images produced via the MR imaging unit 3, a region 9 containing fat in proximity to critical anatomic structures whose temperature must be monitored during therapy is determined in accordance with the invention. Of particular interest is a region 10 of intervening fat in the propagation path of the focused ultrasound beam 11. The HIFU focus is designated by the reference number 12 in FIG. 2. The focus 12 is located within a region of water containing tissue 13. The region 10 is the actual region of interest for the ultrasound thermometry during the therapeutic action. Before treatment commences, a reference ultrasound scan is performed by means of the ultrasound diagnostic unit 5. At periodic intervals during ultrasound heating, successive ultrasound scans are performed. The acquired ultrasound signals are compared with the corresponding signals of the reference scan in order to compute the temperature rise within region 10. As mentioned before, a combined ultrasound and MR thermometry spatial map is presented via display unit 6, thereby illustrating the temperature rise in the fat tissue 9. If a temperature rise above a critical threshold is detected, the user may decide to turn off the therapy. Alternatively, the system may be shut off automatically by means of the corresponding control logic.

Figure 3:
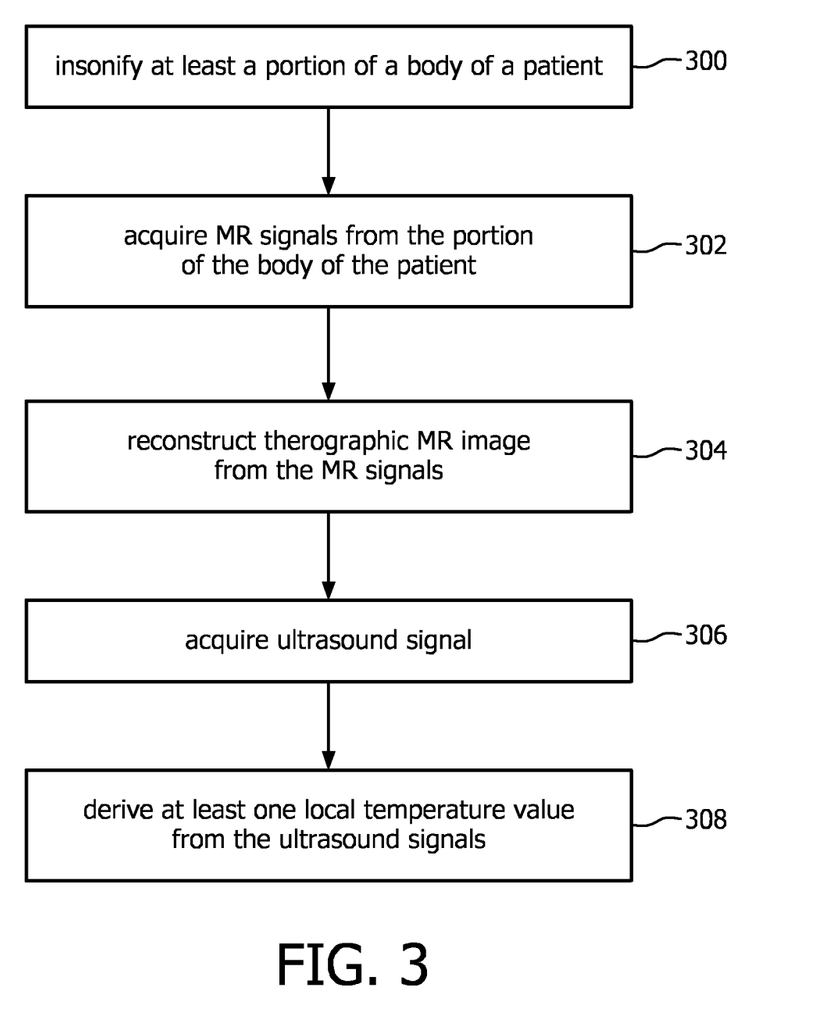
FIG. 3 shows a block diagram which illustrates a method according to an embodiment of the invention.

FIG. 3 shows a block diagram which illustrates a method according to an embodiment of the invention. In step 300 at least a portion of a body of a patient is insonified. In step 302 MR signals from the portion of the body of the patient are acquired. In step 304 a thermographic MR image is reconstructed from the MR signals. In step 306 ultrasound signals are acquired using an ultrasound diagnostic unit. In step 308 at least one local temperature value is derived from the ultrasound signals.

Figure 4:
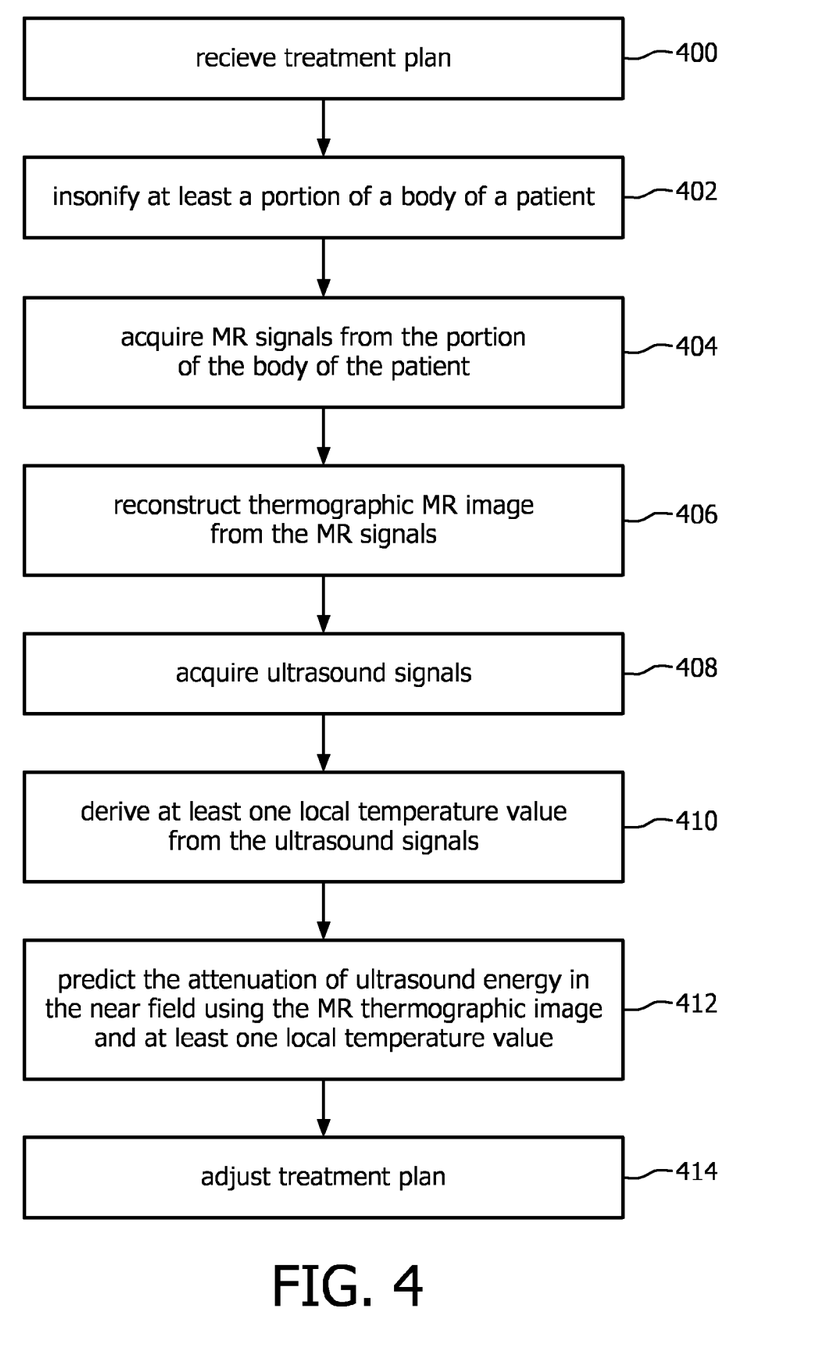
FIG. 4 shows a block diagram which illustrates a further method according to an embodiment of the invention.

FIG. 4 shows a block diagram which illustrates a further method according to an embodiment of the invention. In step 400 a treatment plan is received. The patient may have been imaged using an MR imaging unit previously or some other medical imaging unit. The treatment plan contains information for controlling the operation of the ultrasound therapy unit in reference to the anatomy of the patient. In step 402 at least a portion of a body of a patient is insonified. In step 404 MR signals are acquired from the portion of the body of the patient. In step 406 a thermographic MR image is reconstructed from the MR signals. In step 408 ultrasound signals are acquired using an ultrasonic diagnostic unit. In step 410 at least one local temperature value is derived from the ultrasound signals. In step 412 the attenuation of ultrasound energy in the near field is predicted using the MR thermographic image and that at least one local temperature value. In step 414 the treatment plan is adjusted based on the prediction of the attenuation of ultrasound energy in the near field.

Figure 5:
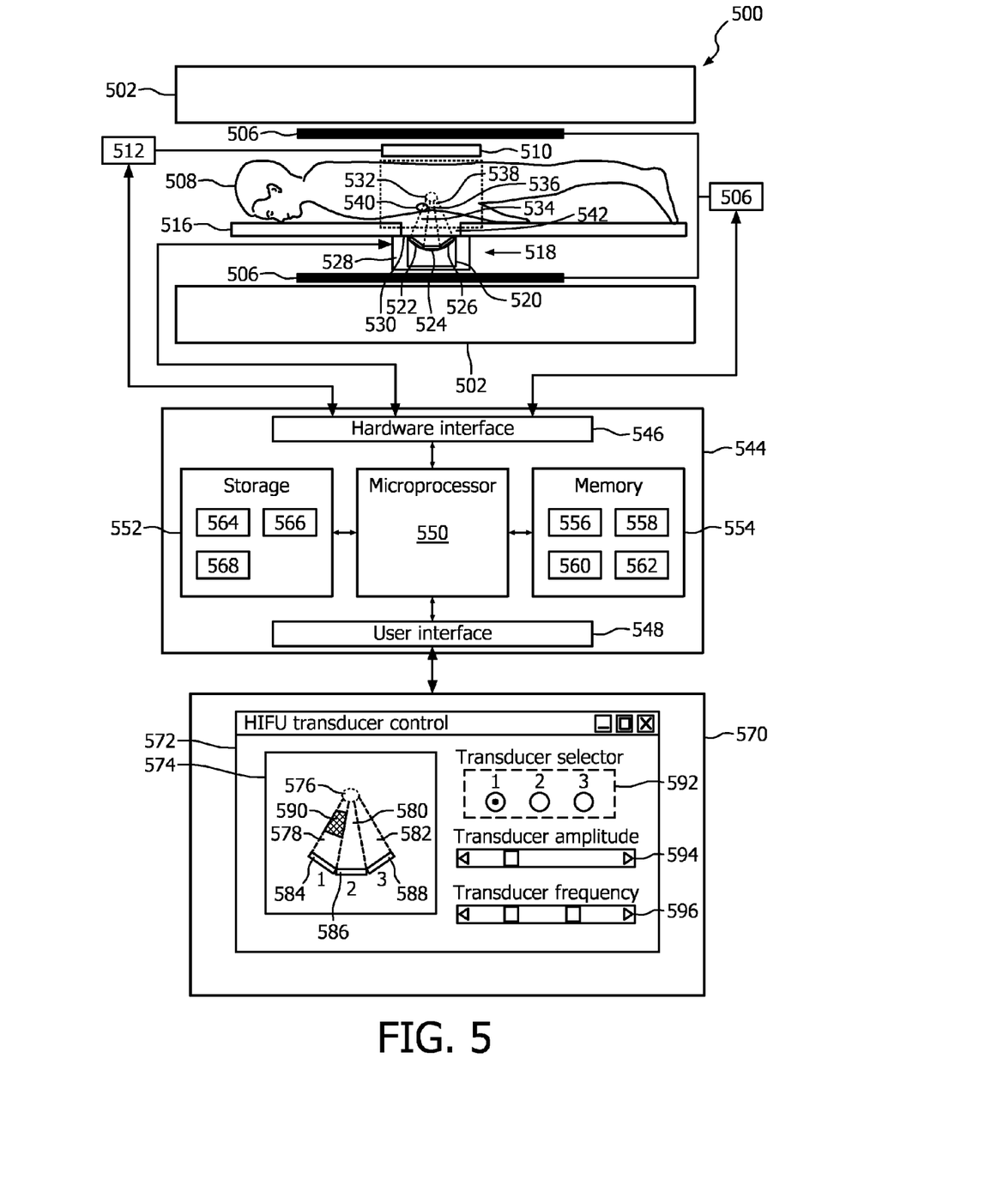
FIG. 5 shows an embodiment of a therapeutic system according to an embodiment of the invention.

FIG. 5 shows an embodiment of a therapeutic system according to an embodiment of the invention. The therapeutic system comprises an MR imaging unit 500. The MR imaging unit 500 comprises a magnet 502 which aligns the spin of nuclei of the patient 508 located within an imaging region 514. Also shown in FIG. 5 is a radio frequency coil 510 which is adapted for emitting and receiving radio frequency signals into the imaging zone 514. In this example only a single radio frequency coil is shown. A single coil may be used for transmitting and receiving or a separate transmit and a separate receive coil may be used. The radio frequency coil is connected to a radio frequency transceiver 512. As with the radio frequency coil 510 separate transmitters and receivers may also be used in place of the radio frequency transceiver. The patient 508 is supported by a patient support 516. Beneath the patient support is an ultrasound therapy unit 518. In this embodiment the ultrasound therapy unit 518 also functions as an ultrasound diagnostic unit.

The ultrasound therapy unit comprises a multi-element ultrasound transducer 520. The multi-element ultrasound transducer 520 has a first ultrasound transducer element 522, a second ultrasound transducer element 524, and a third ultrasound transducer element 526. In practice the multi-element ultrasound transducer would have more than three elements. The multi-element ultrasound transducer 522 is immersed in degassed water 528. The degassed water 528 is adapted for transmitting ultrasound energy emitted by the ultrasound transducer elements 520, 522, 524. The ultrasound therapy unit 518 may also have a mechanical stage adapted for positioning the multi-element ultrasound transducer 520. This mechanism is not shown in this Fig. though. The chamber with the degassed water 528 is sealed by an ultrasound window 530. The ultrasound window is a thin material such as mylar which is adapted for transmitting ultrasound energy. In this way ultrasound energy is able to be conducted from the ultrasound transducer elements 520, 522, 524 to the target zone 532 within the patient 508.

In between the target zone 532 and the first ultrasound transducer element is a first sub-near field region 534. In between the target zone 532 and the second ultrasound transducer element 524 is a second sub-near field region 536. In between the target zone 532 and the third ultrasound transducer element 526 is a third sub-near field region 538. There is an obstruction 540 shown that is in between the target zone 532 and the first ultrasound transducer element 522. That is to say the obstruction 540 is located within the first sub-near field region 534. When ultrasound energy is emitted by the multi-element ultrasound transducer 520 there may be higher than normal heating in the first sub-near field region 534. The increase in temperature may be able to be detected by constructing a thermographic MR image from MR signals acquired within the imaging zone 514.

Also shown is a gel pad 542 which is located within an opening of the patient support 516. The gel pad 542 is adapted for transmitting ultrasonic energy. This forms a means of conducting ultrasonic energy from the ultrasound window 530 to the patient 508. Bubbles may be formed at the interface of the gel pad and the ultrasound window 530 or between the patient 508 and the gel pad 542. In this example the imaging zone extends around the interface between the patient 508 and the gel pad 542. In other embodiments the imaging zone 514 may also extend around the ultrasound window 530.

The radio frequency transceiver 512, gradient coil power supply 506, and ultrasound therapy unit 518 are adapted to be controlled by a computing device 544. The computing device 544 comprises a hardware interface 546 which is adapted for sending and receiving instructions for controlling the radio frequency transceiver 512, the ultrasound therapy unit 518 and the gradient coil power supply 506. The computing device 544 also comprises a user interface 548. The computing device 544 is controlled by a microprocessor 550. A single microprocessor 550 is shown but this also applies to multi-processor systems. Also computing tasks may be divided amongst multiple computing devices 544 or computers. For example image reconstruction or construction of MR thermographic images may be performed by dedicated computer systems. The computing device 544 also comprises storage 552. The computer storage may be any type of machine readable storage. Examples but not limited to are hard drives, floppy drives, USB thumb drives and flash memory hard drives. Microprocessor 550 is also connected to memory 554. This is computer memory which is directly accessible to the microprocessor 550. Located within the memory 554 is a therapeutic system control module.

The control module is a set of computer executable instructions or a computer executable program which comprises instructions for controlling the operation of the therapeutic system. Also located within the memory 554 is a thermographic MR image reconstruction module 558. This contains instructions or a computer executable program for constructing MR signals into magnetic resonance thermographic images. Also located within the memory 554 is an ultrasound temperature analysis module 560. This module contains computer executable instructions or program which when executed analyzes ultrasonic diagnostic signals determining at least one temperature value. Also located within the memory 554 is a treatment plan modification module 562. This module contains instructions or programs which are adapted for predicting the attenuation of ultrasound energy in the near field region and also for modifying the treatment plan if the attenuation of the ultrasound energy in the near field region is greater than a predetermined value. Located within the computer storage 552 is a treatment plan. Located within the computer storage 552 is a thermographic MR image 566. Similarly MR signals could also be stored within the storage 552 or the memory 554. Also located within the storage 568 are one or more programs for operating the therapeutic system.

The user interface 548 is connected to a display 570. The display may be a cathode ray tube, a liquid crystal display, an organic light emitting diode display, a plasma display, or other suitable computer display. Displayed on the display is a graphica user interface 572 for controlling the operation of the ultrasound therapy unit 518. The operator has the option of letting the microprocessor 550 control the operation of the ultrasound therapy unit 518 or to control it manually using the graphical user interface 572. The graphical user interface 572 has a display region 574 for displaying information about the attenuation of ultrasound in the sub-near field regions 534, 536, 538. Within the display region 574 is a representation 576 of the target zone 532. There is also a representation of the 578, 580, 582 of the sub-near field regions 534, 536, 538.

Also shown is a representation 584, 585, 586 of the first 522, second 524, and third 526 ultrasound transducer elements. Visible within the representation 578 of the first sub-near field region 534 is a region 590 which has a prediced attenuation above a predetermined threshold. The region 590 is caused by the obstruction 540. The region 590 may be identified using either the ultrasound diagnostic unit functionality of the ultrasound therapy unit 518 or by a MR therographic image generated by the MR imaging unit 500.

The graphical user interface 572 also comprises a transducer selector 592 which allows an operator to adjust control parameters of a particular ultrasound transducer element. In some embodiments the operator may select an ultrasound transducer element by clicking on the representation of the ultrasound transducer element. The graphical user interface 594 also comprises a control 594 for adjusting the amplitude of the selected ultrasound transducer element. The graphical user interface 594 also comprises a control 596 for adjusting the frequency of the selected ultrasound transducer element. Other embodiments of a graphical user interface may also include a control for deactivating a particular ultrasound transducer element.

Figure 6:
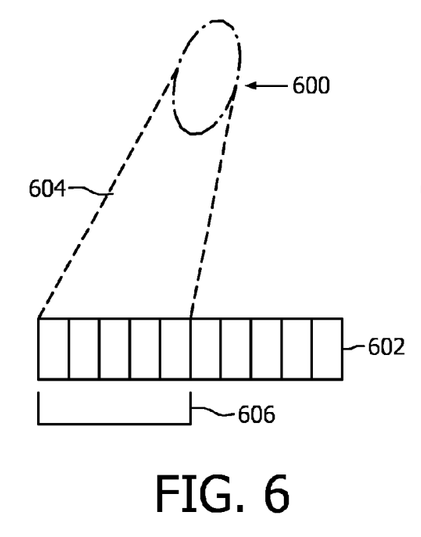
FIG. 6 illustrates a target zone that is targeted for insonification by a multi-element ultrasonic transducer, FIG. 7 illustrated near field heating for the example illustrated in FIG. 6.
Figure 7:
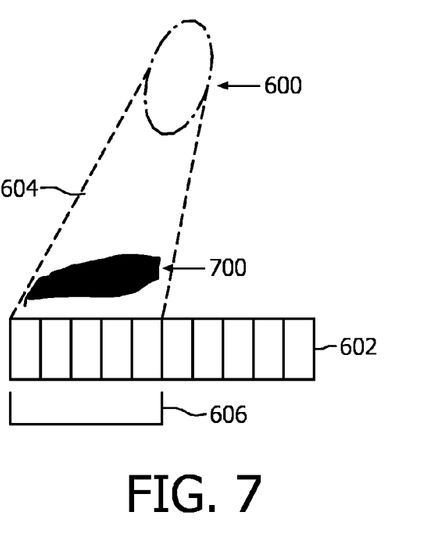
Figure 8:
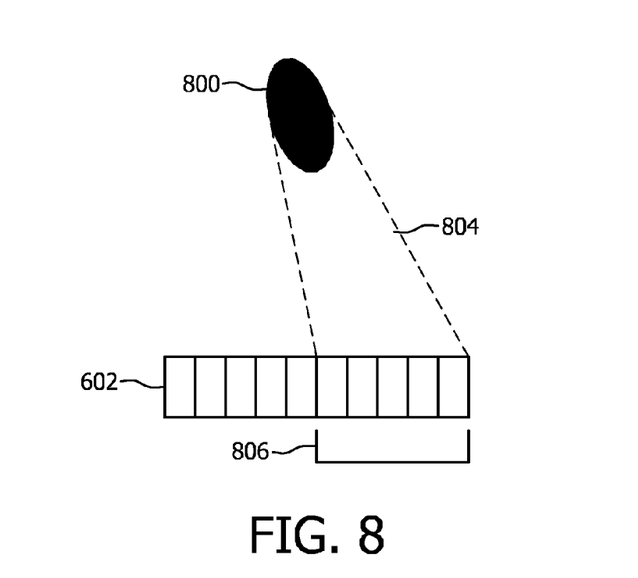
FIG. 8 shows the same example as in FIGS. 6 and 7 with a shifter aperture for the multi-element ultrasounic transducer.

FIGS. 6, 7 and 8 illustrate the adjusting of a treatment plan based upon the prediction of the attenuation of ultrasound energy in the near field region. In FIG. 6 an intended target zone is targeted for insonification by a multi-element ultrasonic transducer 602 that is a linear array of ultrasonic transducers. There is a near field region 604 between the intended target zone 600 and the multi-element ultrasonic transducer 602. A subset of the ultrasonic transducer elements of the multi-element ultrasonic transducer 602 are chosen and form a sub-aperture 606 which was chosen based upon the treatment plan.

FIG. 7 shows the same view as in FIG. 6 except ultrasound energy is produced by the multi-element ultrasonic transducer 602. When this happens near field heating 700 occurs and it is detected using the thermographic MR image and/or the at least one local temperature measurement made by the ultrasound diagnostic unit. The near field heating 700 may be caused by an obstruction which blocks all or a significant portion of the ultrasound or it may be a region which absorbs or attenuates ultrasound greater than was known when the treatment plan was made.

In FIG. 8 it is shown how a change in the aperture 806 allows heating 800 in the intended target zone to occur. The sub-aperture 806 in this example has been shifted and the near field region 804 no longer encompasses the region 700 shown in FIG. 7.

REFERENCE NUMERALS 1 ultrasound therapy unit
2 body
3 MR imaging unit
4 control unit
5 ultrasound diagnostic unit
6 display unit
7 ultrasound imaging probe
8 HIFU transducer
9 region containing fat
10 region of intervining fat
11 focused ultrasound beam
12 HIFU focus
13 water containing tissue
500 MR imaging unit
502 magnet
504 gradient coil 506 gradient coil power supply
508 patient
510 radio frequency coil
512 radio frequency transceiver
514 imaging zone
516 patient support
518 ultrasound therapy unit
520 multi-element ultrasound transducer
522 first ultrasound transducer element
524 second ultrasound transducer element
526 third ultrasound transducer element
528 degassed water
530 ultrasound window
532 target zone
534 first sub-near field region
536 second sub-near field region
538 third sub-near field region
540 obstruction
542 gel pad
544 computing device
546 hardware interface
548 user interface
550 microprocessor
552 storage
554 memory
556 therapeutic system control module
558 thermographic MR image reconstruction module
560 ultrasound temperature analysis module
562 treatment plan modification module
564 treatment plan
566 thermographic MR image
568 one or more programs for operating therapeutic system
570 display
572 graphical user interface
574 display region
576 representation of target zone
578 representation of first sub-near field region
580 representation of second sub-near field region
582 representation of third sub-near field region
584 representation of first ultrasound transducer element
586 representation of second ultrasound transducer element
588 representation of third ultrasound transducer element
590 region with predicted attenuation of ultrasound energy above a predetermined threshold
592 transducer element selector
594 control for transducer element amplitude
596 control for transducer element frequency
600 intended target zone
602 multi-element ultrasonic transducer
604 near field region
606 sub-aperature chosen based upon treatment plan
700 near field heating
800 heating in intended target zone
804 near field region
806 sub-aperature chosen based upon attenuation of ultrasound in near field region

The invention claimed is:

1. Therapeutic system comprising:
an ultrasound therapy unit (1, 518) arranged to insonify at least a portion of a body (2, 508) of a patient with high intensity ultrasound;
a Magnetic Resonance (MR) imaging unit (3, 500) arranged to acquire MR signals from the portion of the body (2, 508) and to reconstruct a thermographic MR image from the MR signals;
an ultrasound diagnostic unit (5, 518) arranged to acquire ultrasound signals from the portion of the body (2, 508) and to derive at least one local temperature value from the ultrasound signals and wherein the MR imaging unit is adapted for acquiring the MR signals from within an imaging zone (514); wherein the ultrasound therapy unit is adapted to insonify a target zone (532) within the patient; wherein the ultrasound therapy unit has a multi-element ultrasonic transducer (520) adapted for focusing ultrasound at the target zone; wherein the therapeutic system further comprises:
a patient support (516) adapted for receiving the patient; wherein the patient support comprises an ultrasound window (530) adapted for transmitting ultrasound from the multi-element ultrasonic transducer to the patient; wherein the ultrasonic transducer has a near field region (534, 536, 538) located between the transducer and the target zone; wherein the imaging zone comprises the near field region; wherein the at least one local temperature value is measured within the near field region;
a computing device (4, 544) for controlling the MR imaging unit; the ultrasound diagnostic unit, and the ultrasonic therapy unit; wherein the computing device comprises one or more processors (550); wherein the computing device further comprises memory (554); wherein the computing device comprises one or more programs (556, 558, 560, 562) stored in the memory; wherein the one or more programs are configured to be executed by the one or more processors; wherein the one or more programs comprise instructions for:
receiving (400) a treatment plan for insonification of the target zone;
predicting (412) the attenuation of ultrasound energy in the near field region using the MR thermographic image and the at least one local temperature; and
adjusting (414) the treatment plan based upon the prediction of the attenuation of ultrasound energy in the near field region.

2. The therapeutic system of claim 1, wherein the near field region comprises sub-near field regions (534, 536, 538); wherein there is a sub-near field region corresponding to each element of the multi-element ultrasonic transducer; and wherein the one or more programs further comprise instructions for predicting (412) the attenuation of ultrasound energy in each of the sub-near field regions using the MR thermographic image and the at least one local temperature.

3. The therapeutic system of claim 2, wherein the one or more programs further comprise instructions for adjusting the frequency of ultrasound energy emitted by each element (522, 524, 526) of the multi-element ultrasonic transducer which is predicted to have an attenuation of ultrasound in a corresponding sub-near field region greater than a predetermined value.

4. The therapeutic system of claim 2, wherein the one or more programs further comprise instructions for adjusting an aperture of the multi-element ultrasonic transducer by reducing the amplitude of ultrasound energy emitted by each element (522, 524, 526) of the multi-element ultrasonic transducer which is predicted to have an attenuation of ultrasound in a corresponding sub-near field region greater than a predetermined value.

5. The therapeutic system of claim 4, wherein the aperture of the multi-element transducer is formed by non-contiguous elements of the multi-element ultrasonic transducer.

6. The therapeutic system of claim 2, further comprising a display adapted for displaying a graphical representation of the multi-element transducer; wherein the display is further adapted for graphically representing the sub field region of each element of the multi-element transducer; wherein the display is adapted for indicating which of the sub field regions is predicted to attenuate ultrasound energy; and wherein the apparatus further comprises a user interface (548) adapted for receiving a selection of the elements of the multi-element transducer for use during insonification of the target zone.

7. The therapeutic system of claim 2, further comprising a signaling element adapted for signaling an operator when an attenuation of the ultrasound in the near field region greater than a predetermined threshold is predicted.

8. The therapeutic system of claim 1, wherein one or more programs further comprise instructions for predicting the attenuation of ultrasound in the near field region by measuring an increase in temperature in the near field region using magnetic resonance thermometry during a test shot of the ultrasonic system.

9. The therapeutic system according to claim 1, wherein the system is arranged to verify the thermographic MR image by using the at least one local temperature value derived from the acquired ultrasound signals.

10. The therapeutic system according to claim 1 wherein
the MR imaging unit (3, 500) is arranged to monitor a spatial temperature distribution within water containing tissue (13) of the portion of the body (2) and
the ultrasound diagnostic unit (5) is arranged to monitor the local temperature within fat tissue (9) of the portion of the body (2).

11. The therapeutic system of claim 1, further comprising a control logic that shuts off the insonification of the ultrasound therapy unit (1) when the local temperature value derived by the ultrasound diagnostic unit (5) exceeds a temperature threshold value.

12. The therapeutic system of claim 1, wherein the ultrasound therapy unit (1) and the ultrasound diagnostic unit (5) share a single ultrasound transducer.

13. The therapeutic system of claim 1, wherein the ultrasound therapy unit is a high intensity focused ultrasound unit (518).

14. The therapeutic system of claim 1, wherein the therapeutic system further comprises a computing device (4, 544) for controlling the MR imaging unit, the ultrasound diagnostic unit, and the ultrasonic therapy unit; wherein the computing device comprises one or more processors (550); wherein the computing device further comprises memory (554); wherein the computing device comprises one or more programs (556, 558, 560, 562) stored in the memory; wherein the one or more programs are configured to be executed by the one or more processors; wherein the one or more programs comprise instructions for:
    insonifing (300) at least a portion of the body of the patient with high intensity ultrasound;
    acquiring (302) MR signals from the portion of the body;
    reconstructing (304) a thermographic MR image from the MR signals;
    acquiring (306) ultrasound signals from the portion of the body; and
    deriving (308) at least one local temperature value from the ultrasound signals.

15. A non-transitory computer-readable storage medium (554) comprising instructions executable by a computing device (544) of a therapeutic system to cause the computing device to perform a method of monitoring during a high intensity ultrasound therapeutic action; wherein the computing device comprises one or more processors (550) for executing the instructions; wherein the therapeutic system comprises an ultrasound therapy unit (1, 518) arranged to insonify at least a portion of a body (2) of a patient with high intensity ultrasound wherein the ultrasound therapy unit is adapted to insonify a target zone (532) within the patient; wherein the ultrasound therapy unit has a multi-element ultrasonic transducer (520) adapted for focusing ultrasound at the target zone; wherein the ultrasonic transducer has a near field region (534, 536, 538) located between the transducer and the target zone; wherein the therapeutic system further comprises a Magnetic Resonance (MR) imaging unit (3, 500) arranged to acquire MR signals from the portion of the body (2) and to reconstruct a thermographic MR image from the MR signals; wherein the therapeutic system further comprises an ultrasound diagnostic unit (5, 518) arranged to acquire ultrasound signals from the portion of the body (2, 508) and to derive at least one local temperature value from the ultrasound signals, the instructions comprising:
    instructions for insonifing (300) the at least a portion of the body of the patient with high intensity ultrasound;
    instructions for acquiring (302) MR signals from a portion of a body of a patient using the MR imaging unit;
    instructions for reconstructing (304) a thermographic MR image from the MR signals;
    instructions for acquiring (306) ultrasound signals from the portion of the body using the ultrasound diagnostic unit; wherein the at least one local temperature value is measured within the near field region;
    instructions for deriving (308) at least one local temperature value from the ultrasound signals
    instructions for receiving (400) a treatment plan for insonification of the target zone;
    instructions for predicting (412) the attenuation of ultrasound energy in the near field region using the MR thermographic image and the at least one local temperature; and
    instructions for adjusting (414) the treatment plan based upon the prediction of the attenuation of ultrasound energy in the near field region.

\* \* \* \* \*